United States Patent [19]

Meul et al.

[11] Patent Number: 5,227,514
[45] Date of Patent: Jul. 13, 1993

[54] SALICYLOYL-CARNITINE AND PROCESS FOR ITS PRODUCTION

[75] Inventors: Thomas Meul, Visp; Jacques Deshusses, Bernex, both of Switzerland

[73] Assignee: Lonza Ltd., Gampel/Valais, Switzerland

[21] Appl. No.: 833,672

[22] Filed: Feb. 11, 1992

[51] Int. Cl.$^5$ ............................................. C07C 69/88
[52] U.S. Cl. .......................................... 560/67; 560/71
[58] Field of Search ............... 560/67, 71; 514/535, 514/540

[56] References Cited

U.S. PATENT DOCUMENTS 4,271,310  6/1981  Watanabe ............................. 560/67
4,336,400  6/1982  Minatoya et al. ..................... 560/66

FOREIGN PATENT DOCUMENTS 7021352  2/1982  Japan .
83/00043  1/1983  World Int. Prop. O. .

OTHER PUBLICATIONS

Okabe et al., Japan. J. Pharmacol., 24, (1974), pp. 363 to 371.
Chaumontet et al., Arzneimittelforschung [Pharmaceutical Agent Research], 28, (1978), pp. 2119 to 2121.

Primary Examiner—Paul J. Killos
Attorney, Agent, or Firm—Fisher, Christen & Sabol

[57] ABSTRACT

Salicylic acid esters of carnitine are distinguished relative to acetylsalicylic acid by high water solubility, low toxicity and good stomach tolerance. The compounds are obtainable in three stages from carnitine hydrochloride and o-methoxybenzoyl chloride.

20 Claims, No Drawings

SALICYLOYL-CARNITINE AND PROCESS FOR ITS PRODUCTION

BACKGROUND OF THE INVENTION

1. Field Of The Invention

The invention relates to 3-(2-hydroxybenzoyloxy)-4-(trimethylammonio)-butyric acid betaine of formula:

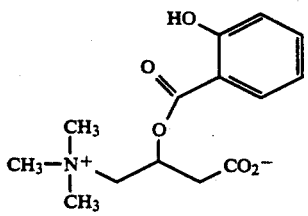

in its racemic form and optically active forms and its pharmaceutically acceptable salts as well as a process for its production. 3-(2-Hydroxybenzoyloxy)-4-(trimethylammonio)-butyric acid betaine is a salicylic acid derivative with therapeutic properties as an ester of the salicylic acid with carnitine (salicyloyl carnitine).

2. Prior Art

Salicylic acid is used in the form of its acetyl derivative to a large extent as an analgesic. Although this acetyl derivative (known, i.a., as Aspirin ®) was originally developed to reduce disturbing side effects of the salicylic acid already known earlier, nevertheless, it is affected by several properties which limit its possibilities of use. Above all, its low water solubility, in particular in an acid medium, for example, in gastric juice, is one of these unfavorable properties. With oral administration of aqueous solutions, the low solubility can lead to the precipitation of the active ingredient in the stomach. This effect is undesirable not only in individuals with a sensitive or previously damaged gastric mucous membrane, since it can lead to serious side effects in these individuals, but it quite generally slows down the resorption and, thus, also the beginning of the analgesic action.

Moreover, acetylsalicylic acid can be administered practically only orally, but not parenterally, for example, intravenously, intraperitoneally or topically. But precisely because of the quick onset of action and/or the gentle treatment of the gastrointestinal tract, a parenteral administration would often be desirable.

BROAD DESCRIPTION OF THE INVENTION

The main object of the invention was to provide a salicylic acid derivative, which is also readily water-soluble in the acid range, is easily resorbed, exhibits a lowest possible toxicity and can be administered both orally and parenterally or topically and shows a quickly starting analgesic action in all forms of administration. The main object of the invention is achieved: by 3-(2-hydroxybenzoyloxy)-4-(trimethylammonio)-butyric acid betaine:

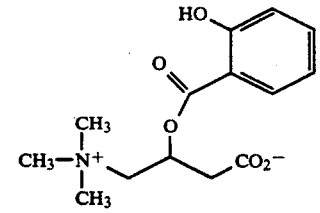

and the pharmaceutically acceptable salts thereof; by (R)-(−)-3-(2-hydroxybenzoyloxy)-4-(trimethylammonio)butyric acid betaine:

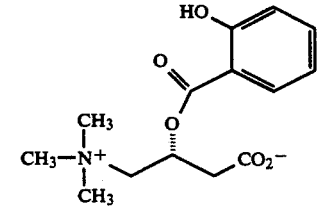

and the pharmaceutically acceptable salts thereof; and by (S)-(+)-3-(2-hydroxybenzoyloxy)-4-(trimethylammonio)-butyric acid betaine:

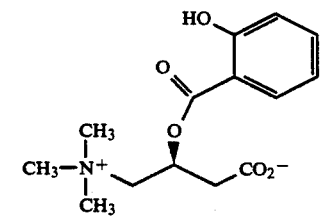

and the pharmaceutically acceptable salts thereof.

Other objects and advantages of the invention are set out herein or are obvious herefrom to one skilled in the art. The other objects and advantages of the invention are achieved by the compounds and process of the invention.

The invention also involves the process of administering a pharmaceutical composition containing: 3-(2-hydroxybenzoyloxy)-4-(trimethylammonio)-butyric acid betaine or its pharmaceutically acceptable salts for use as the therapeutic active ingredient; or (R)-(−)-3-(2-hydroxybenzoyloxy)-4-(trimethylammonio)-butyric acid betaine or its pharmaceutically acceptable salts for use as the therapeutic active ingredient; or (S)-(+)-3-(2-hydroxybenzoyloxy)-4-(trimethylammonio)-butyric acid betaine or its pharmaceutically acceptable salts for use as the therapeutic active ingredient.

The invention also involves the process of administering a pharmaceutical composition containing: 3-(2-hydroxybenzoyloxy)-4-(trimethylammonio)-butyric acid betaine or its pharmaceutically acceptable salts for use as an analgesic which is gentle to the gastric mucous membrane; or (R)-(−)-3-(2-hydroxybenzoyloxy)-4-(trimethylammonio)-butyric acid betaine or its pharmaceutically acceptable salts for use as an analgesic which is gentle to the gastric mucous membrane; or (S)-(+)-3-(2-hydroxybenzoyloxy)-4-(trimethylammonio)-butyric acid betaine or its pharmaceutically acceptable salts for use as an analgesic which is gentle to the gastric mucous membrane.

The invention also involves: 3-(2-methoxybenzoyloxy)-4-(trimethylammonio)-butyric acid betaine and its salts; and (R)-(−)-3-(2-methoxybenzoyloxy)-4-(trimethylammonio)-butyric acid betaine and its salts; and (S)-(+)-3-(2-methoxybenzoyloxy)-4-(trimethylammonio)-butyric acid betaine and its salts.

The invention further involves a process for the production of 3-(2-hydroxybenzoyloxy)-4-(trimethylammonio)butyric acid betaine. The process includes esterifying a 3-hydroxy-4-(trimethylammonio)-butyric acid betaine hydrohalide in a first stage with a 2-methoxybenzoyl halide to a 3-(2-methoxybenzoyloxy)-4-(trimethylammonio)-butyric acid betaine hydrohalide. The intermediate compound is demethylated with hydrobromic acid in acetic acid to 3-(2-hydroxybenzoyloxy)-4-(trimethylammonio)-butyric acid betaine hydrobromide. The latter compound is deprotonated with a base to the betaine product. Preferably the 3-hydroxy-4-(trimethylammonio)-butyric acid betaine hydrohalide is the hydrobromide thereof. Preferably the 2-methoxybenzoyl halide is the acid chloride thereof. Preferably a weakly basic anion exchanger is used as the base Preferably a (R)-2-hydroxy-4-(trimethylammonio)-butyric acid betaine hydrohalide (L-carnitine hydrohalide) is used as the initial material.

DETAILED DESCRIPTION OF THE INVENTION

The invention includes 3-(2-hydroxybenzoyloxy)-4-(trimethylammonio)-butyric acid betaine. The betaine compound comprises an asymmetrical carbon atom and can, therefore, occur in two mirror image, optically active forms and as a racemic mixture. Here, the enantiomer with (R)-configuration, which is derived from the naturally occurring L-carnitine, is preferred. But the advantageous physical-chemical properties, such as, high water solubility and advantageous pH of the solution, are also achieved by the (S)-enantiomer and the racemate. However, L-carnitine is known as an acyl group carrier in lipo-metabolism. It is actively taken up by highly affine transport systems in most organs of the body and by antiport transporters in cellular organelles (mitochondria, etc.). It is to be assumed that salicyloyl-L-carnitine is also taken up in cells and organelles by these transport systems and, thus, the onset of action is even accelerated.

Acyl-L-carnitines are further easily cleaved by cell-specific enzymes, so that a quick release of the salicylate radical is to be expected.

Tests in rats showed an extremely low acute toxicity of salicyloyl-L-carnitine. Doses up to 1000 mg/kg of body weight were easily orally tolerated and no harmful side effects were observed in intravenous and intraperitoneal administration of therapeutic amounts. In a first study, the analgesic action of salicyloyl-L-carnitine was compared with that of aspirin after oral, intraperitoneal and intravenous administration in rats. In oral administration, salicyloyl-L-carnitine showed an action slowed up about 1.5 hours in comparison with acetylsalicylic acid, in intraperitoneal and intravenous administration, a marked analgesic action started already after 10 to 15 minutes.

Of course, it is also within the scope of the invention to form salts of the salicyloyl-carnitine with pharmaceutically acceptable acids and to use the compound in this form.

The salicyloyl-carnitine is produced according to the invention in that a carnitine hydrohalide, preferably hydrochloride, is esterified first with a 2-methoxybenzoyl halide [o-anisoyl halide], preferably acid chloride, to the corresponding 3-(2-methoxybenzoyloxy)-4-(trimethylammonio)butyric acid betaine hydrohalide [o-anisoylcarnitine hydrohalide]. As a solvent for the esterification step, suitably a polar protic solvent is used, which is inert toward hydrogen chloride. Advantageously, low aliphatic carboxylic acids, such as, acetic acid or formic acid, are used for this purpose; trichloroacetic acid is especially preferred. The reaction temperature in the solvent is advantageously 50° to 90° C., the reaction time is 1 to 4 hours. The solvent can be used in the subsequent process steps.

By subsequent treatment with an excess of hydrobromic acid in glacial acetic acid, the methoxy group can be converted to a hydroxy group. The reaction with hydrobromic acid is suitably performed at 20° to 80° C. In this case, the target compound is obtained by the hydrobromic acid excess in the form of hydrobromide, which can be isolated in crystalline form.

For the use for pharmaceutical purposes, the hydrobromide is suitably converted with a base to the free betaine. For reasons of solubility, this is achieved advantageously by treatment with a weakly basic anion exchanger resin. In the use, also possible in principle, of a dissolved base, namely, a salt would develop, which shows solubility behavior similar to betaine and, therefore, would not be easy to separate it. A weakly basic anion exchanger, which has primary, secondary or tertiary amino groups as functional groups, has the advantage, moreover, that it neither hydrolyzes the ester group of the product nor binds the latter by the weakly acid phenol function.

The invention process is suitable, of course, depending on the initial material, equally for the production of racemic and of optically active salicyloyl-carnitine.

Also, it is within the scope of the process according to the invention to then convert the betaine by adding a pharmaceutically acceptable acid to a corresponding salt.

The following examples illustrate the performance of the production process according to the invention.

EXAMPLE 1

(R)-(−)-3-(2-Methoxybenzoyloxy1-4-(trimethylammonio)-butyric acid betaine hydrochloride [o-anisoyl-L-carnitine hydrochloride]

61.8 g of L-carnitine hydrochloride was dissolved in 152.0 g of trichloroacetic acid at 80° C. Within 30 minutes, 80.0 g of 2-methoxybenzoyl chloride was instilled at 80° C. The reaction mixture was stirred for another 90 minutes at the same temperature, cooled to 30° C. and mixed with stirring with 500 ml of diethyl ether and 200 ml of ethyl acetate. The mixture was refluxed for 30 minutes, and the product crystallized out. The crude product was filtered off and dried (crude yield was 112.6 g), then suspended in 200 ml of isopropanol at 80° C., filtered and washed twice from the filter with 50 ml of isopropanol each. The yield of 75.7 g (73.0 percent) of colorless crystals. Other properties of the product were:

Melting point: 186° to 190° C.
$[\alpha]_D^{20} = -28.8°(c=1, \text{water})$ $^1$H—NMR (DMSO—d$_6$, 300 MHz) δ7.02–7.75 (m, 4H) 5.67–5.75 (m, 1H) 3.78–4.02 (m, 2H) 3.84 (s, 3H) 3.22 (s, 9H) 2.80–2.90 (m, 2H)

EXAMPLE 2

(R)-(−)-3-(2-Hydroxybenzoyloxy)-4-(trimethylammonio)-butyric acid betaine hydrobromide [salicyloyl-L-carnitine hydrobromide].

24.0 g of o-anisoyl-L-carnitine hydrochloride (produced according to Example 1) was dissolved in 200 ml of a 30 percent solution of hydrobromic acid in glacial acetic acid and stirred for 6 hours at 60° C. Then, the reaction mixture was concentrated by evaporation in a vacuum, and the residue was suspended with 200 ml of diethyl ether and filtered. The crystalline crude product was recrystallized twice from 110 ml each of hot isopropanol. The yield was 14.0 g (50.2 percent) of colorless crystals. Other properties of the product were:

Melting point: 173° to 175° C.
$[\alpha]_D^{20} = -27.2°(c=1, water)$

EXAMPLE 3

(R)-(−)-3-(2-Hydroxybenzoyloxy)-4-(trimethylammonio)-butyric acid betaine [salicyloyl-L-carnitine]

13.0 g of salicyloyl-L-carnitine hydrobromide (produced according to Example 2) was dissolved in 130 ml of water. The solution was filtered by a column with 58 g of a weakly basic anion exchanger resin (Amberlite ® IRA-93) and concentrated by evaporation in a vacuum. The product was precipitated by adding 60 ml of acetone. The crystalline product was filtered off and dried at 40° C. in a vacuum. The yield was 10.0 g (quantitative) of colorless crystals. Other properties of the product were:

Melting point: 120° to 122° C.
$[\alpha]_D^{20} = 25.0°(c=1, water)$
Elementary analysis: Cld. C 59.5; H 6.9; N 4.9; Br -; Cl -; Fnd. C 59.8; H 6.8; N 5.0 Br <0.1; Cl <0.1.

Stomach tolerance tests in rats (Ulcer Index)

R-(−)-3-(2-Hydroxybenzoyloxy)-4-(trimethylammonio)butyric acid betaine [salicyloyl-L-carnitine=SC] was tested in comparison with acetylsalicylic acid [ASA] in male rats, by gastric mucous membrane changes being induced according to the methods of Okabe et al., Japan. J. Pharmacol. 24, (1974), pages 363 to 371. The test substances were administered p.o. in a 1 percent carboxymethyl cellulose suspension (1 percent CMC) to the test rats. The gastric mucous membrane changes were measured by the Ulcer Index according to Chaumontet et al., Arzneimittelforschung [Pharmaceutical Agent Research], 28, (1978), pages 2119 to 2121. Table 1 describes the results.

TABLE 1

| Substance | Ulcer Index (U.I.) | Number of rats |
|---|---|---|
| Comparison, 1% CMC 1 ml/250 g | 63.00 | 10 |
| Comparison, ASA 200 mg · kg$^{-1}$ | 300.00 | 20 |
| Invention, SC 200 mg · kg$^{-1}$ | 144.00 | 10 |
| Invention, SC 500 mg · kg$^{-1}$ | 200.00 | 10 |
| Invention, | 200.00 | 10 |

TABLE 1-continued

| Substance | Ulcer Index (U.I.) | Number of rats |
|---|---|---|
| SC 1000 mg · kg$^{-1}$ | | |

CMC = carboxymethyl cellulose
ASA = acetylsalicylic acid
SC = salicyloyl-L-carnitine

What is claimed is:

1. 3-(2-Hydroxybenzoyloxy)-4-(trimethylammonio)-butyric acid betaine:

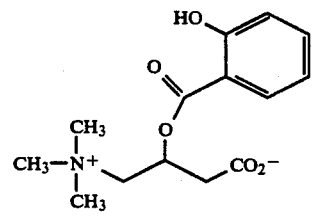

or a pharmaceutically acceptable salt thereof.

2. (R)-(−)-3-(2-Hydroxybenzoyloxy)-4-(trimethylammonio)butyric acid betaine:

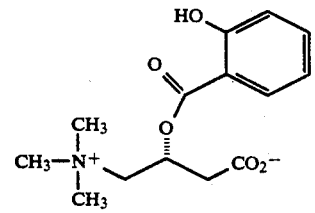

or a pharmaceutically acceptable salt thereof.

3. (S)-(+)-3-(2-Hydroxybenzoyloxy)-4-(trimethylammonio)butyric acid betaine:

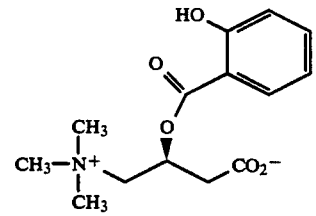

or a pharmaceutically acceptable salt thereof.

4. Process comprising administering a pharmaceutical composition containing 3-(2-hydroxybenzoyloxy)-4-(trimethylammonio)-butyric acid betaine or a pharmaceutically acceptable salt thereof as a therapeutically active analgesic ingredient and water as a carrier.

5. Process comprising administering a pharmaceutical composition containing (R)-(−)-3-(2-hydroxybenzoyloxy)-4-(trimethylammonio)-butyric acid betaine or a pharmaceutically acceptable salt thereof as a therapeutically active analgesic ingredient and water as a carrier.

6. Process comprising administering a pharmaceutical composition containing (S)-(+)-3-(2-hydroxybenzoyloxy)-4-(trimethylammonio)-butyric acid betaine or a pharmaceutically acceptable salt thereof as a therapeutically active analgesic ingredient and water as a carrier.

7. Process comprising administering a pharmaceutical composition containing 3-(2-hydroxybenzoyloxy)-4-(trimethylammonio)-butyric acid betaine or a pharmaceutically acceptable salt thereof as an analgesic.

8. Process comprising administering a pharmaceutical composition containing (R)-(−)-3-(2-hydroxybenzoyloxy)-4-(trimethylammonio)-butyric acid betaine or a pharmaceutically acceptable salt thereof as an analgesic.

9. Process comprising administering a pharmaceutical composition containing (S)-(+)-3-(2-hydroxybenzoyloxy)-4-(trimethylammonio)-butyric acid betaine or a pharmaceutically acceptable salt thereof as an analgesic.

10. 3-(2-Methoxybenzoyloxy)-4-(trimethylammonio)-butyric acid betaine or a salt thereof.

11. (R)-(−)-3-(2-Methoxybenzoyloxy)-4-(trimethylammonio)-butyric acid betaine or a salt thereof.

12. (S)-(+)-3-(2-Methoxybenzoyloxy)-4-(trimethylammonio)-butyric acid betaine or a salt thereof.

13. Process for the production of 3-(2-hydroxybenzoyloxy)-4-(trimethylammonio)-butyric acid betaine comprising esterifying a 3-hydroxy-4-(trimethylammonio)-butyric acid betaine hydrohalide with a 2-methoxybenzoyl halide to a 3-(2-methoxybenzoyloxy)-4-(trimethylammonio)-butyric acid betaine hydrohalide, demethylating the 3-(2-methoxybenzoyloxy)-4-(trimethylammonio)-butyric acid betaine hydrohalide with hydrobromic acid in acetic acid to 3-(2-hydroxybenzoyloxy)-4-(trimethylammonio)-butyric acid betaine hydrobromide and deprotonating 3-(2-hydroxybenzoyloxy)-4-(trimethoxyammonio)-butyric acid betaine hydrobromide with a base to 3-(2-hydroxybenzoyloxy)-4-(trimethylammonio)-butyric acid betaine.

14. Process according to claim 13 wherein the 3-hydroxy-4-(trimethylammonio)-butyric acid betaine hydrohalide which is 3-hydroxy-4-(trimethylammonio)-butyric acid betaine hydrochloride.

15. Process according to claim 14 wherein the 2-methoxybenzoyl halide is 2-methoxybenzoyl acid chloride.

16. Process according to claim 15 wherein a weakly basic anion exchanger is used as the base.

17. Process according to claim 16 wherein an (R)-2-hydroxy-4-(trimethylammonio)-butyric acid betaine hydrohalide [an L-carnitine hydrohalide] is used as the 3-hydroxy-4-(trimethylammonio)-butyric acid betaine.

18. Process according to claim 13 wherein the 2-methoxybenzoyl halide is 2-methoxybenzoyl acid chloride.

19. Process according to claim 13 wherein a weakly basic anion exchanger is used as the base.

20. Process according to claim 13 wherein an (R)-2-hydroxy-4-(trimethylammonio)-butyric acid betaine hydrohalide [an L-carnitine hydrohalide] is used as the 3-hydroxy-4-(trimethylammonio)-butyric acid betaine.

* * * * *